(12) United States Patent
Mukhopadhyay et al.

(10) Patent No.: US 7,659,434 B2
(45) Date of Patent: Feb. 9, 2010

(54) METHOD FOR PRODUCING FLUORINATED ORGANIC COMPOUNDS

(75) Inventors: Sudip Mukhopadhyay, Williamsville, NY (US); Haridasan K. Nair, Williamsville, NY (US); Hsueh S. Tung, Getzville, NY (US); Michael Van Der Puy, Amherst, NY (US); Daniel C. Merkel, West Seneca, NY (US); Rajesh K. Dubey, Williamsville, NY (US); Jing Ji Ma, West Seneca, NY (US); Barbara A. Light, Niagara Falls, NY (US); Kim M. Fleming, Hamburg, NY (US); Cheryl L. Bortz, N. Tonawanda, NY (US); Richard Udy, Niagara Falls, NY (US)

(73) Assignee: Honeywell International Inc., Morristown, NJ (US)

( * ) Notice: Subject to any disclaimer, the term of this patent is extended or adjusted under 35 U.S.C. 154(b) by 237 days.

(21) Appl. No.: 11/592,415

(22) Filed: Nov. 3, 2006

(65) Prior Publication Data

US 2007/0112228 A1  May 17, 2007

Related U.S. Application Data

(63) Continuation-in-part of application No. 11/118,504, filed on Apr. 29, 2005, now Pat. No. 7,371,904, and a continuation-in-part of application No. 11/118,503, filed on Apr. 29, 2005, now Pat. No. 7,345,209, and a continuation-in-part of application No. 11/118,530, filed on Apr. 29, 2005, now Pat. No. 7,189,884.

(60) Provisional application No. 60/567,426, filed on Apr. 29, 2004, provisional application No. 60/567,429, filed on Apr. 29, 2004, provisional application No. 60/567,425, filed on Apr. 29, 2004, provisional application No. 60/567,428, filed on Apr. 29, 2004, provisional application No. 60/733,444, filed on Nov. 3, 2005, provisional application No. 60/733,383, filed on Nov. 3, 2005, provisional application No. 60/567,427, filed on Apr. 29, 2004.

(51) Int. Cl.
  *C07C 21/18* (2006.01)
(52) U.S. Cl. .................. 570/136; 570/375; 570/156
(58) Field of Classification Search .................. None
  See application file for complete search history.

(56) References Cited

U.S. PATENT DOCUMENTS

| 2,931,840 A | 4/1960 | Marquis |
|---|---|---|
| 2,996,555 A | 8/1961 | Rausch |
| 3,472,826 A | 10/1969 | Potts et al. |
| 3,659,023 A | 4/1972 | Regan |
| 4,086,407 A | 4/1978 | Fozzard |
| 4,798,818 A | 1/1989 | Baizer et al. |
| 4,900,874 A | 2/1990 | Ihara et al. |
| 5,162,594 A | 11/1992 | Krespan |
| 5,532,419 A | 7/1996 | Van Der Puy et al. |
| 5,545,777 A | 8/1996 | Morikawa et al. |
| 5,574,192 A | 11/1996 | Van Der Puy et al. |
| 5,679,875 A | 10/1997 | Aoyama et al. |
| 5,710,382 A | 1/1998 | Dunmead et al. |
| 5,969,198 A | 10/1999 | Thenappan et al. |
| 5,986,151 A | 11/1999 | Van Der Puy |
| 6,023,004 A | 2/2000 | Thenappan et al. |
| 6,031,141 A | 2/2000 | Mallikarjuna Rao et al. |
| 6,066,769 A | 5/2000 | Nappa et al. |
| 6,111,150 A | 8/2000 | Sakyu et al. |
| 6,369,284 B1 | 4/2002 | Nappa et al. |
| 6,548,719 B1 | 4/2003 | Nair et al. |
| 6,809,226 B1 | 10/2004 | Pennetreau et al. |
| 6,958,424 B1 | 10/2005 | Nair et al. |
| 6,977,316 B1 | 12/2005 | Mukhopadhyay et al. |
| 7,026,520 B1 | 4/2006 | Mukhopadhyay et al. |
| 7,026,521 B1 | 4/2006 | Mukhopadhyay et al. |
| 7,071,367 B1 | 7/2006 | Mukhopadhyay et al. |
| 7,132,578 B1 | 11/2006 | Mukhopadhyay et al. |
| 7,135,601 B2 | 11/2006 | Mukhopadhyay et al. |
| 7,189,884 B2 | 3/2007 | Mukhopadhyay et al. |
| 7,196,236 B2 | 3/2007 | Mukhopadhyay et al. |
| 2003/0060670 A1 | 3/2003 | Nair et al. |
| 2004/0119047 A1 | 6/2004 | Singh et al. |
| 2005/0020862 A1 | 1/2005 | Tung et al. |
| 2005/0080302 A1 | 4/2005 | Baker et al. |

(Continued)

FOREIGN PATENT DOCUMENTS

EP        0522639        1/1993

(Continued)

OTHER PUBLICATIONS

Henne et al Journal of American Chemical Society, 1946, v68, pp. 496-497.*

(Continued)

*Primary Examiner*—Karl J Puttlitz
*Assistant Examiner*—Yevegeny Valenrod

(57) ABSTRACT

A method for preparing fluorinated organic compounds comprising contacting hydrogen fluoride with at least one compound of formula I:

$$CX_3CXYCH_3 \qquad\qquad I$$

where each X is independently Cl, I or Br, and each Y is independently H or F, said contacting step being carried out under conditions effective to produce a compound of formula II $$CF_3CZCH_2 \qquad\qquad II$$

where Z is Cl, I, Br, or F.

34 Claims, No Drawings

U.S. PATENT DOCUMENTS

| | | | |
|---|---|---|---|
| 2005/0090698 | A1 | 4/2005 | Merkel et al. |
| 2005/0171391 | A1 | 8/2005 | Janssens et al. |
| 2007/0112227 | A1 | 5/2007 | Mukhopadhyay et al. |
| 2007/0112229 | A1 | 5/2007 | Mukhopadhyay et al. |
| 2007/0112230 | A1 | 5/2007 | Mukhopadhyay et al. |
| 2007/0129580 | A1 | 6/2007 | Mukhopadhyay et al. |

FOREIGN PATENT DOCUMENTS

| | | |
|---|---|---|
| EP | 0644173 | 3/1995 |
| EP | 974571 A2 | 1/2000 |
| GB | 844597 A | 8/1960 |
| JP | 11140002 | 5/1999 |
| JP | 2000169404 | 6/2000 |
| JP | 2000178543 | 6/2000 |
| WO | WO9008752 A | 8/1990 |
| WO | 9504021 | 2/1995 |
| WO | 96/01797 A | 1/1996 |
| WO | 98/42645 | 3/1998 |
| WO | 98/21171 | 5/1998 |
| WO | 99/48993 | 9/1999 |
| WO | 00/39242 | 7/2000 |
| WO | 01/07384 | 2/2001 |
| WO | 03027051 | 4/2003 |
| WO | 2005/012212 | 2/2005 |
| WO | 2005/042451 A | 5/2005 |
| WO | 2005108332 | 11/2005 |
| WO | 2005108334 | 11/2005 |
| WO | 2007019355 A | 2/2007 |

OTHER PUBLICATIONS

Mcbee et al Journal of American Chemical Society, 1947, v69, pp. 944-947.*

Henne, Albert L., et. al., Chlorinated Derivatives of 2-Fluoropropane J. American Chemical Society, Jul. 11, 1941; pp. 2692-2694; vol. 63.

Database WPI Week 199812, AN 1998-126110, XP002427152, Derwent Publications Ltd., London, GB & JP 10 007605A (Central Glass Co LTD) Jan. 13, 1998, abstract.

March, J., Advanced Organic Chemistry,, 1997, pp. 631-636, McGraw-Hill International Book Company, XP002427150.

Banks, et. al., Journal of Fluorine Chemistry, vol. 82, Issue 2, pp. 171-174 (1997).

Database Beilstein, Beilstein Institute For Organic Chemistry, M. Van Der Puy: J. Fluorine Chemistry, vol. 81, No. 2, 1997, pp. 187-192 XP002424669.

Database Beilstein, Beilstein Institute For Organic Chemistry, Haszeldine, Steele: J. Chem. Soc. 1953, p. 1592, 1597, XP0022424670.

Database Beilstein, XP002426121.

Dickson, R.S., Fluorcarbon-Aluminium Compounds, Aust. J. Chem., 1972, 25, 761-8.

Gambareto et al., "The Reaction of chlorine monofloride with unsaturated compounds", 1976, XP00246119.

Haszeldine R.N., Free-radical Additions to Unsaturated Systems. Part XVII. Reaction of Trifluoroiodomethane with Mixtures of Ethylene and Vinyl Fluoride and of Ethylene and Propene, Journal of Chemical Society, Section C: (3), 414-21. p. 415, 1970.

J Burdon et al.: J. Fluorine Chemistry, vol. 40, pp. 283-318, XP002424668, 1988.

Knunyants, I. L. et al, Reaction of Fluoro Olefins, Institute of Heteroorganic Compounds, Bulletin of the Academy of Sciences of USSR, Division of Chemical Sciences—ISSN 0568-5230, p. 1312-1317, 1960.

Kunshenko B V et al.: Reaction of Organic Compounds with SF4-HF-Hallogenating System VII, 1992, XP002344564.

Vittorio Minanari, A Novel Systensis of Perhalogenated Alkenes, J. Org. Chem. 1992, 57, 5018-5019.

Henne, A. and Flanagan, J., "Fluorinated Derivatives of Propane", Journal of American Chemical Society, 65, (1943) 2362.

Henne, A. and Renoll, M., "Fluorinated Derivatives of Propane", Journal of American Chemical Society, 59, (1937) 2434.

* cited by examiner

METHOD FOR PRODUCING FLUORINATED ORGANIC COMPOUNDS

CROSS-REFERENCES TO RELATED APPLICATIONS

This application is claiming the priority benefit of U.S. Provisional Application No. 60/733,444 filed Nov. 3, 2005 and of U.S. Provisional Application No. 60/733,383 filed Nov. 3, 2005. This application is also is a Continuation-in-Part of U.S. patent application Ser. No. 11/118,503, (pending) filed on Apr. 29, 2005, which in turn claims the priority benefit of U.S. Provisional Patent Application Nos. 60/567,427 and 60/567,425 filed Apr. 16, 2004.

This application is also a Continuation-in-Part of U.S. patent application Ser. No. 11/118,504, (pending) filed on Apr. 29, 2005, which in turn claims the priority benefit of U.S. Provisional Patent Application Nos. 60/567,426 and 60/567,429 filed Apr. 16, 2004.

This application is also a Continuation-in-Part of U.S. patent application Ser. No. 11/118,530, (pending) filed on Apr. 29, 2005, which in turn claims the priority benefit of U.S. Provisional Patent Application No. 60/567,428.

The disclosures of each of the above-mentioned applications are incorporated herein by reference. Also incorporated herein by reference are the following U.S. Applications 60/733,378; 60/733,355; 60/733,383; 60/733,377 and 60/733,379, each of which was filed on Nov. 3, 2005.

BACKGROUND (1) Field of the Invention

This invention relates to novel methods for preparing fluorinated organic compounds, and more particularly to methods of producing fluorinated olefins.

(2) Description of Related Art

Hydrofluorocarbons (HFC's), in particular hydrofluoroalkenes such as tetrafluoropropenes (including 2,3,3,3-tetrafluoro-1-propene (HFO-1234yf)) have been disclosed to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFCs do not contain chlorine and thus pose no threat to the ozone layer.

Several methods of preparing hydrofluoroalkanes are known. For example, U.S. Pat. No. 4,900,874 (Ihara et al) describes a method of making fluorine containing olefins by contacting hydrogen gas with fluorinated alcohols. U.S. Pat. No. 2,931,840 (Marquis) describes a method of making fluorine containing olefins by pyrolysis of methyl chloride and tetrafluoroethylene or chlorodifluoromethane. The preparation of HFO-1234yf from trifluoroacetylacetone and sulfur tetrafluoride has been described. See Banks, et al., *Journal of Fluorine Chemistry*, Vol. 82, Iss. 2, p. 171-174 (1997). Also, U.S. Pat. No. 5,162,594 (Krespan) discloses a process wherein tetrafluoroethylene is reacted with another fluorinated ethylene in the liquid phase to produce a polyfluoroolefin product.

Notwithstanding prior teachings, applicants have come to appreciate a continuing need for methods of efficiently preparing certain hydrofluorocarbons, particularly tetrafluorpropenes such as HFO-1234yf.

SUMMARY OF THE INVENTION

Applicants have developed methods for producing fluorinated organic compounds, including hydrofluoropropenes, which preferably comprises contacting at least one compound of the formula $(X_aY_{1-a})F$ with at least one compound of formula (I):

$$CX_3CXYCH_3 \quad (I)$$

where each X is independently Cl, I or Br, each Y is independently H or F and a is 0 or 1.

The preferred contacting step of the present invention is carried out under conditions effective to produce a compound of formula (II)

$$CF_3CZ=CH_2 \quad (II)$$

where Z is Cl, I, Br, or F.

In certain preferred embodiments the contacting step produces a reaction product comprising tetrafluoropropene, and in particular 2,3,3,3-tetrafluoro-1-propene (HFO-1234yf).

The contacting step preferably comprises reacting a compound of formula (I) with at least one compound of the formula $(X_aY_{1-a})F$, such as HF, in the gas phase in the presence of a catalyst. In preferred embodiments, the conversion of the compound of formula I in the reaction is from about 70% to about 100%. In certain embodiments, including those which produce conversion levels as indicated herein, the selectivity of the reaction to tetrafluoropropene, and to HFO-1234yf in particular, is from about 5 to about 40%. In certain preferred embodiments the reaction product also contains a trifluor-monochloropropene, particularly 2-chloro, 3,3,3,trifluoro-1-propoene (HFO-1233xf) with a selectivity of from about 50% to about 90%.

DETAILED DESCRIPTION OF PREFERRED EMBODIMENTS

One beneficial aspect of the present invention is that it enables the production of desirable fluroolefins, preferably C3 fluoroolefins, from relatively low cost and readily obtainable starting materials. More specifically, certain preferred embodiments of the present invention involve producing the desired C3 fluoroolefin from C3 olefin's, such as propylene. Propylene is in many embodiments an advantageous starting material because it is relatively inexpensive, is relatively easy to handle, and is generally readily available in commercial quantities.

Thus, in certain embodiments the present methods include the step of reacting C3 olefin, such as propylene, with a halogenating agent (such as ClF or HF) under conditions effective to produce a compound of formula (III)

$$CH_{3-n}X_nCXYCH_3 \quad (III)$$

where n is 0, 1 or 2. This reaction is sometimes referred to herein for convenience but not necessarily by way of limitation, as a halogen addition reaction.

Preferably, the compound of formula (III) is then reacted, preferably in a photo-chlorination reaction, to produce a reaction product containing at least one compound of formula (I) as described above. Preferably the formula (I) compound is then exposed to reaction conditions, which are sometimes referred to herein for convenience, but not necessarily by way of limitation, as fluorination to produce a reaction product containing one or more of the desired fluorolefins. Preferred aspects of each of these preferred steps is described below, with the titles used as headings for these steps being used for convenience but not necessarily by way of limitation.

A. Reaction of C3 Olefin with Halogenating Agent

In preferred embodiments, a compound of formula (IV)

$$CH_nX_{3-n}CHC=CH_2 \quad (IV)$$

is contacted under reaction conditions with a compound of formula $X_mY_{2-m}$ wherein X, Y are as defined above, provided that the compound is not $H_2$, and m is 0, 1, or 2, to produce a compound of formula (III), namely, $CH_nX_{3-n}CXYCH_3$ where n is 0, 1 or 2. In preferred embodiments, the compound of formula (IV) is propylene (n is 3 and X is H) and the compound of formula $X_mY_{2-m}$ is one or more of ClF, $Cl_2$, $F_2$ and HF, preferably one or more of ClF, $Cl_2$, and HF. The compound $X_mY_{2-m}$, and compounds which perform a similar function in the present reactions, are referred to herein as halogenation agents.

In certain preferred embodiments, the contacting step comprises contacting, (preferably by introducing into a reactor) the compounds in an halogenation agent:formula (IV) mole ratio of from about 1:1 to about 4:1, and even more preferably of from about 2:1 to about 4:1. In preferred embodiments in which the compound of $X_mY_{2-m}$ comprises HF and the formula (IV) compound comprises propylene, the HF:propylene mole ratio of the feeds to the reactor are from about 1:1 to about 10:1 and even more preferably from about 2:1 to about 4:1. In preferred embodiments in which the compound of $X_mY_{2-m}$ comprises ClF (X is Cl, Y is F, and m is 1) and the formula (IV) compound comprises propylene, the ClF:propylene mole ratio of the feeds to the reactor are from about 10 to about 0.1 and even more preferably from about 1 to about 0.2. In preferred embodiments in which the compound of $X_mY_{2-m}$ comprises $Cl_2$ (m is 2 and X is Cl) and the formula (IV) compound comprises propylene, the $Cl_2$:propylene mole ratio of the feeds to the reactor are from about 5 to about 0.1 and even more preferably from about 1 to about 0.2.

This reaction step can be carried out in the liquid phase and/or in the gas phase, and it is contemplated that the reaction can be carried out batch wise, continuous, or a combination of these.

1. Liquid Phase Halogen Addition Reactions

Although not necessarily preferred, certain embodiments of the present invention (particularly when the $X_mY_{2-m}$ compound is ClF, HF or $Cl_2$, or combinations of two or more of these) involve relatively low temperature reactions in which at least the organic reactant(s) are charged to the reactor as liquids, with the reactor preferably maintained at a temperature of from about −90° C. to about −50° C., and at least a portion of the reaction is carried in the liquid phase (the normal boiling point $H_nX_{3-n}$ of the preferred reactant propylene is −47.8° C.). However, it is contemplated that at least some portion of the reaction product may be produced and/or removed from the reaction mixture in such embodiments as a gaseous material.

For those preferred embodiments which utilize ClF as a reactant, it is sometimes preferred to provide ClF, preferably in situ, by the liquid-phase reaction of HF and $Cl_2$ in the presence of catalyst, preferably a transition metal catalyst, and even more preferably a transition metal halide catalysts such as FeCl3, TaCl5, TiCl4, SbCl5, SbCl3, and CrCl3, SbF3, SbF5, AlF3, and CrF3, and combinations of two or more of these. In certain preferred embodiments, therefore, the present halogenation step comprises contacting CH3CH=CH2, HF and Cl2 in the presence of a metal catalyst, preferably a metal chloride salt, preferably with addition of kinetic energy to provide a substantially uniform reaction mixture (such as stirring), under conditions effective to form a reaction product comprising the desired compound of formula (III).

In certain preferred embodiments, the reaction is carried out at a temperature of from about −90° C. to about −50° C., more preferably from about −80° C. to about −70° C., under conditions effective to achieve a percentage conversion of at least about 70%, more preferably at least about 90%, and even more preferably at least about 100% of the compound of formula (IV). Preferably, the reaction conditions are effective to achieve a percentage selectivity to compounds of formula (III), and preferably 2-fuoropropane, of at least about 50%, more preferably at least about 75%, and even more preferably at least about 95%. In certain preferred embodiments a selectivity of about 98% or greater is achieved.

As used herein, the term "percentage conversion" with respect to a reactant refers to the moles reacted in the reaction process divided by the moles of reactant in the feed to the process multiplied by 100.

As used herein, the term "percentage selectivity" with respect to an organic reaction product refers to the ratio of the moles of that reaction product to the total of the remaining organic reaction products multiplied by 100.

In certain preferred embodiments the reaction time for the preferred liquid phase halogenation reaction is from about 1 to about 3 hours. The reaction product in preferred embodiments includes one or more of $CH_3CHFCH_2Cl$, $CH_3CHClCH_2Cl$, $CH_3CHClCH_2Cl$, and/or $CH_3CHFCH_3$. In preferred embodiments, the reaction product comprises from about 40 wt. % to about 75 wt. % $CH_3CHFCH_2Cl$, from about 5 to about 35 wt. % $CH_3CHClCH_2Cl$, from about 5 to about 15 wt % $CH_3CHClCH_2Cl$, and less than about 5% $CH_3CHFCH_3$.

It will be appreciated that many alternatives for the provision of ClF in accordance with this preferred step of the present invention are available and within the scope hereof. By way of example, the reactant ClF may be provided in certain embodiments simply by purchasing the needed quantity of the material in the appropriate form. In other preferred embodiments, it is desirable to provide the ClF by conducting a liquid-phase Reaction of HF and $Cl_2$, preferably in the presence of transition metal halide such as $SbF_5$. Such reactions, especially single stage reactions, can be achieved using any equipment and conditions known and available in the art for such types of reactions, preferably at a temperature of from about −50° C. to −90° C., and even more preferably the reaction temperature is maintained at a temperature of from about −65° C. to about −85° C.

In certain embodiments, a two stage reaction may be used, with the first stage being a gas phase reaction and the second stage being a liquid phase reaction. In such embodiments the ClF produced in this first reaction stage, and/or from other sources, is preferably then charged to a second reaction vessel or to a second region of the same vessel, preferably a second autoclave, where it is contacted with a compound of formula (IV), such as propylene, at a temperature as specified above, preferably at about −75° C., and preferably under conditions capable of providing selectivity to a compound of formula (III0, preferably $CH_3CHFCH_2Cl$, of at least about 60% and up to about 75% or greater.

2. Gas/Liquid Phase Halogen Addition Reactions

Although not necessarily preferred, the formation of a compound of formula III may also be carried out at least partially in a gas phase reaction, preferably in the presence of a catalyst. For example, high conversion and selectivity can be achieved in some embodiments by first reacting HF and $Cl_2$ in a liquid phase, and preferably in a continuous liquid phase reaction, by charging the reactor with a catalyst, preferably a transition metal halide such as $SbF_5$ and conducting the reaction at a temperature of from about −50° C. to 50° C. to produce ClF. In such embodiments it is preferred to introduce the ClF produced in the gas phase, together with a compound of formula (IV), into a liquid phase reactor, generally in accordance with the conditions described above, to produce a compound of formula (III), preferably at a selectivity to $CH_3CHFCH_2Cl$ of at least about 60%, and even more preferably at least about 70%.

3. Preferred Gas Phase Halogenation Reactions

For certain preferred embodiments, particularly those preferred embodiments which utilize HF as a reactant, it is preferred to provide a compound of formula (III) by a gas-phase Reaction of HF and a compound of formula (IV) in the presence of catalyst, preferably a transition metal catalyst, and even more preferably a transition metal halide catalysts such as $FeCl_3$, $TaCl_5$, $TiCl_4$, $SbCl_5$, $SbCl_3$, and $CrCl_3$, $SbF_3$, $SbF_5$, $AlF_3$, and $CrF_3$, and combinations of two or more of these. In certain preferred embodiments, therefore, the preferred halogenation step comprises contacting $CH_3CH=CH_2$, preferably an iron based catalyst, and even more preferable an iron chloride catalyst, and maintaining the reactor temperature at from about 20° C. to about 100° C., more preferably from about 25° C. to about 35° C., with a preferred reactor pressure of from about 15 to about 200 psia, and even more preferably from about 20 to about 100 psia. In such preferred embodiments HF is preferably charged to the reactor, preferably as a liquid (for example by maintaining the vessel containing the HF under pressure, such as 45 psig of $N_2$ head space pressure) and the compound of formula (IV) is charged to the reactor, preferably as a gas. In such embodiments the conversion of the formula (IV) compound, particularly propylene, is preferably at least about 40%, more preferably at least about 80%, and selectivity to compounds of formula (III), particularly 2-fluoropropane, is preferably at least about 40%, more preferably at least about 60%, more preferably at least about 80%, and in certain embodiments at least about 90%. In certain preferred embodiments selectivity of about 95% is preferred. Examples of other catalysts that may be used in this aspect of the invention include carbon, carbon nanotubes, $SbCl_5C$, $SbF_5/C$, $FeCl_3$, $CrF_3$, Cr-oxyfluoride, and $Cr_2O_3$.

B. Chlorination of the Compound of Formula III

According to preferred aspects of this invention, a compound of formula (III), preferably but not necessarily produced in accordance with the procedures described above, is chlorinated to produce a compound of formula (I), namely, $CX_3CXYCH_3$ where each X is independently Cl, I or Br, and each Y is independently H or F. In its broad aspects, the preferred chlorination step is amenable to a large number of specific processing condition and steps in accordance with the teachings contained herein, and all such variations are within the broad scope of the present invention. It is particularly preferred, however, that the chlorination step comprise photochlorination. Thus, the preferred reaction step comprises exposing the reactants, preferably in a liquid phase, to ultraviolet radiation, preferably in the range of from about 200 to about 400 nm. The chlorination agent preferably comprises chlorine gas, either neat or preferably with a diluent such as nitrogen. A chorination catalyst, such as $V_2O_5$, Zeolites, and $Au/TiO_2$ catalyst, may be used in certain embodiments. The reaction is preferably carried out at a temperature of from about −20° C. to about 200° C., and even more preferably from about 25° C. to about 120° C. for a time of from about 5 seconds to about 5 hours, more preferably from about 15 seconds to about 30 min. The reaction product, which comprises a compound of formula (I), may then optionally be subject to one or more separation steps, such as distillation, to remove unwanted byproducts and produce a stream relatively concentrated in compounds of the formula (I).

C. Chlorination of the Compound of Formula II

The methods of the present invention preferably comprise reacting a compound of formula (I) with a fluorinating agent to produce a fluoroolefin, preferably a C3 fluoroolefin, more preferably a compound of formula (II), and even more preferably tetrafluoropropene. This preferred reaction step may be described, by way of illustration but not necessarily by way of limitation, by the following reaction equation in connection with embodiments in which the compound of formula (I) is tetrafluormonochloropropane and the fluorinating agent is hydrogen fluoride:

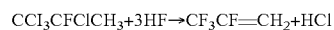

$$CCl_3CFClCH_3 + 3HF \rightarrow CF_3CF=CH_2 + HCl$$

This aspect of the present invention is sometimes referred to herein as a fluorination reaction. In many aspect of such preferred embodiments, $CF_3CCl=CH_2$ (HFO-1233xf) is also produced in the reaction.

It is contemplated that this reaction step may be preformed using a wide variety of process parameters and process conditions in view of the overall teachings contained herein. For example, it is contemplated that certain embodiments may comprise a liquid phase, non-catalytic reaction. However, it is generally preferred that this reaction step comprise a gas phase catalyzed reaction, preferably a metal catalyst, and even more preferably one or more transition metal-based catalysts (including in certain preferred embodiments transition metal halide catalysts), such as $FeCl_3$, chromiumoxyfluoride, Ni (including Ni mesh), $NiCl_2$, $CrF_3$. Other catalysts include carbon-based catalysts, antimony-based catalysts (such as $Sb/Cl_5$), aluminum-based catalyst (such as $AlF_3$ and $AlO_3$). Many other catalysts may be used, including palladium-based catalyst, platinum-based catalysts, Rhodium-based catalysts and ruthenium-based catalysts. Of course, two or more any of these catalysts, or other catalysts not named here, may be used in combination.

In general it is preferred that the catalysts are pretreated by fluorination prior to use. In preferred embodiments, fluorination of the catalysts comprises exposing the catalyst to a stream of HF at about reaction temperature and pressure.

In certain preferred embodiments, the present step of fluorinating a compound of formula I to produce a compound of formula II comprises contacting a the formula I compound with a fluorinating agent, preferably under conditions effective to provide a formula I conversion of at least about 10%, more preferably at least about 55%, and even more preferably at least about 70%. In certain preferred embodiments the conversion is at least about 90%, and more preferably about 100%. Furthermore, in certain preferred embodiments, the present step of fluorinating a compound of formula I to produce a compound of formula II is conducted under conditions effective to provide a formula II selectivity of at least about 5%, more preferably at least about 20%, more preferably at least about 50%, and even more preferably at least about 90%. In embodiments in which the compound of formula I comprises $CCl_3CFClCH_3$ (HCFC-241bb), the selectivity to HFO-1234yf is at least about 5%, more preferably at least about 10%, more preferably at least about 50% or higher, and the selectivity to HFO-1233xf is at least about 5%, more preferably from about 30% to about 70%, and even more preferably from about 40% to about 60%.

EXAMPLES

Additional features of the present invention are provided in the following examples, which should not be construed as limiting the claims in any way.

Examples 1-24

These examples illustrate gas phase fluorination-dehydrohalogenation of $CCl_3CFClCH_3$ (241bb) to $CF_3CCl=CH_2$ (12334) and $CF_3CF=CH_2$ (1234yf). A 22-inch (½-inch diameter) Monel tube reactor is charged with 120 cc of catalyst, as specified in Table I below. All catalysts are fluorinated for 6 h with 80 g/h of HF at reaction temperature under 20 psig pressure. The reactor is mounted inside a heater with three zones (top, middle and bottom). The reactor temperature is monitored using a 5-point thermocouples kept at the middle inside of the reactor. The inlet of the reactor is connected to a pre-heater, which is kept at about 300° C. by electrical heating. Liquid HF is fed from a cylinder into the pre-heater through a needle valve, liquid mass-flow meter, and a control valve at a constant flow of 1-1000 g/h. The HF cylinder is kept at a constant pressure of about 40 psig by applying anhydrous $N_2$ gas pressure into the cylinder head space. 10-120 g/h of organic compound of formula I (HCFC-241bb) is fed from a cylinder kept at about 145° C. through a regulator, needle valve, and a gas mass-flow-meter. The compound of formula I is also fed time to time as liquid at 120° C. from a cylinder into the pre-heater through a needle valve, liquid mass-flow meter, and a control valve at a constant flow of 50-150 g/h. The organic line from the cylinder to the pre-heater is kept at 265° C. by wrapping with constant temperature heat trace and electrical heating. All feed cylinders are mounted on scales to monitor their weight by difference. The reactions are run at a constant reactor pressure of about 0-100 psig by controlling the flow of reactor exit gases by another control valve. The gases exiting the reactor are analyzed by on-line GC and GC/MS connected through a hotbox valve arrangement to prevent condensation. The product was collected by flowing the reactor exit gases through a 20-60 wt % aq. KOH scrubber solution and then trapping the exit gases from the scrubber into a cylinder kept in dry ice or liquid $N_2$. The products were then isolated by distillation. The results are shown in Table I below.

TABLE 1

$CCl_3CFClCH_3 + 3HF \rightarrow CF_3CF=CH_2 + HCl$

| Example#/Catalyst | T, C | % Conversion of 241bb | % Selectivity to 1234yf | % Selectivity to 1233xf | % Selectivity 1234yf/1233xf |
|---|---|---|---|---|---|
| Example 1/Chromium Oxoxyfluoride | 250 | 56 | 1 | 12 | 0.08 |
| Example 2/(Plant Catalyst) | 320 | 92 | 7 | 85 | 0.08 |
| Example 3/(Plant Catalyst) | 350 | 96 | 8 | 69 | 0.11 |
| Example 4/(Plant Catalyst) | 375 | 100 | 12 | 63 | 0.19 |
| Example 5/4-6 wt % FeCl3/C | 50 | Plugged | | | |
| Example 6/(NORIT-RFC-3) | 100 | Plugged | | | |
| Example 7 | 120 | 100 | 14 | 57 | 0.25 |
| Example 8 | 150 | 100 | 14 | 61 | 0.23 |
| Example 9 | 200 | 100 | 11 | 54 | 0.2 |
| Example 10 | 220 | 100 | 9 | 43 | 0.2 |
| Example 11/Carbon | 300 | 56 | 11 | 26 | 0.42 |
| Example 12/Carbon | 400 | 71 | 9 | 17 | 0.53 |
| Example 13/Carbon | 500 | 89 | 5 | 14 | 0.36 |
| Example 14/Ni-mesh | 250 | 42 | 7 | 29 | 0.24 |
| Example 15/Ni-mesh | 350 | 84 | 10 | 62 | 0.16 |
| Example 16/Ni-mesh | 425 | 100 | 14 | 53 | 0.26 |
| Example 17/25 wt % SbCls/C | 110@50 psig | 100 | 18 | 59 | 0.3 |
| Example 18/25 wt % SbCls/C | 120@50 psig | 100 | 21 | 49 | 0.42 |
| Example 19/1.4 wt % NiC12/Al2O3 | 250 | | | | |
| Example 20/1.4 wt % NiC12/Al2O3 | 320 | 92 | 14 | 62 | 0.22 |
| Example 21/1.4 wt % NiC12/Al2O3 | 350 | | | | |
| Example 22/1.4 wt % Ni/Al2O3 | 350 | 100 | 6 | 52 | 0.12 |
| Example 23/AlF3 | 150 | 82 | 0 | 8 | 0 |
| Example 24/CrF3 | 200 | 89 | 2 | 11 | 0.18 |

In addition to the products identified in the table, other compounds produced in the reaction are 1,1,1-trifluoroethane (143a), 3-chloro-2,2,3,3-tetrafluoropropane(244cc), 3,3-dichloro-2,2,3-trifluoropropane(243cc), 1-propene-1,1-dichloro-2-fluoro, 2,3,3-trichloro-2-fluoropropane(251bb), 1-chloro-3,3,3-trifluoro-1-propene (1233zd), 3,3,3-trifluoro-1-propene (1243zf), 1,1-dichloro-2-fluoro-1-propene,2,3,3-trichloro-2-fluoropropane, dichlorodifluoropropene, and carbon black.

Example 25

This example illustrates addition of $F_2$ to $CH_3CH=CH_2$ in a liquid phase reaction, which is illustrated by the following reaction scheme:

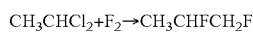
$$CH_3CHCl_2 + F_2 \rightarrow CH_3CHFCH_2F$$

About 1-100 wt % $F_2$ in nitrogen is bubbled through 125 g of liquid propylene in a stirred Hastrelloy C reactor at about −50° C. to −75° C. for about 1 hour in the presence of HF as the solvent. A 1 gallon Parr reactor is first charged with a relatively inert solvent, HF, to help with heat transfer and dilution of the organic. Then 125 grams of propylene are added batch wise to the reactor. The reaction mixture is continuously mixed and cooled to the desired temperature. Then the $F_2$ feed (1 wt %), diluted with N2 (99 wt %), is introduced continuously directly into the reaction mixture through a dip tube until about 90% of the stoichiometric amount needed to convert all the propylene that is added. The reactor temperature and pressure are controlled automatically at the desired set points of between −50 to −75° C. and a constant pressure of 40 psig. The temperatures are chosen to minimize the amount of propylene that would exit the reactor with the $N_2$ diluent. The gases exiting the reactor are passed through a caustic scrubber carboy and an activated alumina column to remove acidity, then a dri-rite column to remove moisture, and finally the organic is collected in a DIT. When the desired amount of $F_2$ is added the reaction liquid is sampled. The sample is absorbed in $H_2O$ and the organic is recovered by phase separation. The organic is then analyzed by GC and GC/MS. The remaining material in the reactor is boiled off through the scrubbing system and the organic is collected in the DIT and analyzed by GC and GC/MS. The analyses are used to determine that the reaction has an overall selectivity to $CH_3CHFCH_2F$ of about 36-45%.

Example 26

This example illustrates addition of $F_2$ to $CH_3CH=CH_2$ in a gas phase reaction, which is illustrated by the following reaction scheme:

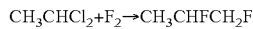
$$CH_3CHCl_2 + F_2 \rightarrow CH_3CHFCH_2F$$

The same apparatus as described in Example 25 is used, except that gaseous propylene and 1% F2 (99% dilution w/N2) are fed into the Parr reactor via a common dip tube. Propylene is fed at a 50% stoichiometric excess. The reactor is kept at 70° C. and at atmospheric pressure. The reactor effluent is passed through a DIT, which collected most of the organic. Only a couple of grams of vapor are left in the Parr reactor at the end of the experiment. GC analysis of the material indicated about 10% conversion of the propylene. The selectivity to $CH_3CHFCH_2F$ is about 32% based on GC area %.

Example 27

This example illustrates addition of F2 to CH3CH=CH2 in a gas phase reaction under the same conditions as Example 26, except the reaction is performed at higher temperature of about 0 to −20° C. A yield of about 10% $CF_3CHFCH_2F$ is obtained, which is then transformed to HFO-1234yf with 100% selectivity in the next step by reacting with 20% KOH solution in the presence of 18-crown ether as the phase-transfer catalyst at about 55° C. using a 300 ml autoclave.

Example 28

This example illustrates addition of fluorine to $CH_3CH=CH_2$ in a gas phase reaction, which is illustrated by the following reaction scheme:

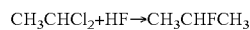
$$CH_3CHCl_2 + HF \rightarrow CH_3CHFCH_3$$

In a gas-phase reaction a Monel tube reactor was charged with 1909 cc of 4-6-wt % $FeCl_3/C$ (NORIT-RFC 3, commercial catalyst from NORIT NEDERLAND B.V.). The reactor was mounted in a constant temperature sand-bath with 40-50 ml/min of air flowing through the sand-bath. The sand-bath set point was set at 28° C. during the reaction. The inlet of the reactor was connected to a pre-heater which was kept at 106° C. by supplying 30 psig steam through the jacket. The liquid-HF was fed from a cylinder into the pre-heater through a positive displacement pump and kept at a constant flow of 15.88 mol/h (318 g/h) by controlling the flow with a research control valve. The HF cylinder was kept at a constant pressure of 30-40 psig by applying anhydrous $N_2$ gas pressure into the cylinder head space. A 5.4 mol/h (227 g/h) of propylene is fed as a gas from a cylinder through a regulator, needle valve, and flow controller directly into the reactor inlet at a point just after the pre-heater. HF and Propylene cylinders were mounted on two different scales to monitor their weight by difference. The reactions were run at a constant reactor pressure of 25 psig by controlling the flow of reactor exit gases by another research control valve. The mole ratio of HF to Propylene was kept at 2.94 with a contact time of 33 sec. The exit gases coming out of the reactor were analyzed by an on-line GC and GCMS connected through a hotbox valve arrangements to prevent condensation. The conversion of Propylene was almost 100% and the selectivity to 2-Fluoropropane was 98%. The reaction was performed continuously over 4 days period and the catalyst did not loose any activity. The product was collected by flowing the reactor exit gases through a 20-60 wt % aq. KOH scrubber solution and then trapping them in a cylinder kept inside dry ice or liquid $N_2$.

Examples 29-42

This example illustrates the chlorination of 2-fluoropropane ($CH_3CHFCH_3$) to CCl3CFClCH3 (241bb) in a gas phase reaction, which is illustrated by the following reaction scheme:

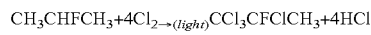
$$CH_3CHFCH_3 + 4Cl_2 \xrightarrow{(light)} CCl_3CFClCH_3 + 4HCl$$

A 500 ml Pyrex reactor was placed inside a Rayonet photo chlorinator at room temperature (25° C.). The reactor used in this study was a RAYONET Model-RPR-100 with standard-operating temperature of 35° C. and standard power con sumption around 400 watts. The inside of the photo chlorinator was equipped with 16 UV-lamps; the number of lamps could be varied easily. The 2-Fluoropropane was fed into the reactor from a cylinder kept at a constant water bath temperature of 35° C. through a regulator and mass-flowcontroller. Chlorine gas was fed from a cylinder through a regulator, needle valve, and a massflow-controller into the reactor. $N_2$ was used as the diluents, though the reaction proceeds well without it from a cylinder, which was fed from a cylinder through regulator and mass-flowcontroller. A fan at the bottom of the photo chlorinator was kept on with a constant flow of $N_2$ to helped keeping the reactor at a constant temperature. This was because of fast dissipation of heat of reaction to avoid run-away reaction. The products that were high boiling liquids stayed inside the reactor collection section, collected and analyzed after the stipulated reaction time. The exit gases out of the reactor was analyzed by on-line GC which contains mainly unreacted 2-fluoropropane, N2 and mono-chlorinated products. The liquid products thus obtained was then washed with water to remove HCl and soluble Chlorine and then purified by distillation under vacuum. The experimental mp of 241bb is 98-101° C. and boiling is 139° C. The purity was around 95-100%. The results are shown in Table 2 below.

TABLE 2

Photo chlorination of 2-Fluoropopane (R281ea) to $CCl_3CFClCH_3$ (241bb)

| Ex # | FP, Sccm | $Cl_2$, sccm | $N_2$, sccm | Contact time, sec | Mole ratio of $Cl_2$ to FP | T, h | Lamp | % Conversion | % Sel. to $CCl_3CF ClCH_3$ | % Overall sel. |
|---|---|---|---|---|---|---|---|---|---|---|
| 29 | 20 | 96 | 0 | 206 | 4.8 | 2 | 8 | 48 | 18 | 49 |
| 30 | 20 | 80 | 0 | 239 | 4 | 2 | 8 | 52 | 29 | 62 |
| 31 | 20 | 80 | 50 | 159 | 4 | 1 | 8 | 54 | 38 | 71 |
| 32 | 20 | 80 | 100 | 120 | 4 | 1 | 8 | 46 | 19 | 63 |
| 33 | 20 | 120 | 50 | 126 | 6 | 1 | 8 | 75 | 35 | 69 |
| 34 | 20 | 150 | 50 | 108 | 7.5 | 1 | 8 | 34 | 19 | 81 |
| 35 | 20 | 20 | 76 | 206 | 1 | 1 | 8 | 27 | 26 | 85 |
| 36 | 20 | 40 | 56 | 206 | 2 | 1 | 8 | 35 | 20 | 81 |
| 37 | 20 | 60 | 36 | 206 | 3 | 1 | 8 | 35 | 28 | 82 |
| 38 | 20 | 80 | 16 | 206 | 4 | 1 | 8 | 42 | 32 | 74 |
| 39 | 20 | 96 | 0 | 206 | 4.8 | 1 | 8 | 50 | 42 | 73 |
| 40 | 20 | 96 | 0 | 206 | 4.8 | 0.25 | 8 | 45 | 35 | 70 |
| 41 | 20 | 96 | 0 | 206 | 4.8 | 0.5 | 8 | 40 | 37 | 76 |
| 42 | 20 | 96 | 0 | 206 | 4.8 | 0.75 | 8 | 54 | 41 | 71 |

FP is 2-Fluoropropane; sccm is standard cubic centimeter per minute; total volume of the reactor in contact with the light is 450 ml (Pyrex);Conversion is the ratio of moles of FP converted to products to total moles of FP fed; Selectivity to $CCl_3CFClCH_3$ is the ratio of moles of FP converted to $CCl_3CFClCH_3$ to total moles of FP reacted;Overall selectivity is the ratio of moles of FP converted to $CH_3CFClCH_3$, $ClCH_2CFClCH3$, $Cl_2CHCFClCH3$, and $CCl_3CFClCH_3$ to total moles of FP reacted. There are total 16 lamps.The reactor is a BAYONET-Model-RPR-100, standard operating temperature 35° C. and standard power consumption 400 watts.

Examples 43-72

This example illustrates the photochlorination of 2-fluoropropane ($CH_3CHFCH_3$) to $CCl_3CFClCH_3$ (241 bb) in a gas phase reaction as described in Examples 29-42, except 4 parameters are varied, including flow rates of $Cl_2$ and 2-Fluoropropane, time of irradiation, and number of lamps at room temperature. The results are reported in Table 3 below:

TABLE 3

Photo chlorination of 2-Fluoropopane to $CCl_3CFClCH_3$

| Ex # | $Cl_2$, Sccm | 2-FP, sccm | Time, min | No of lamps | $N_2$, sccm | Contact time, sec | Mole ratio of $Cl_2$ to 2-FP | % 2-FP Conversion | % Sel. to $CCl_3CFClCH_3$ | % Overall sel. to mono-, di-, tri- and tetra-chloro compound S |
|---|---|---|---|---|---|---|---|---|---|---|
| 43 | 80 | 40 | 20 | 4 | 25 | 165 | 2 | 65 | 57 | 68 |
| 44 | 80 | 20 | 20 | 4 | 25 | 191 | 4 | 70 | 44 | 74 |
| 45 | 50 | 30 | 30 | 6 | 25 | 228 | 1.7 | 31 | 54 | 67 |
| 46 | 50 | 30 | 30 | 6 | 25 | 228 | 1.7 | 31 | 54 | 67 |
| 47 | 20 | 20 | 20 | 4 | 25 | 367 | 1 | 54 | 24 | 90 |
| 48 | 20 | 40 | 20 | 8 | 25 | 281 | 0.5 | 34 | 14 | 87 |
| 49 | 20 | 40 | 40 | 4 | 25 | 281 | 0.5 | 33 | 18 | 93 |
| 50 | 80 | 40 | 40 | 8 | 25 | 281 | 0.5 | 54 | 48 | 57 |
| 51 | 80 | 40 | 20 | 8 | 25 | 165 | 2 | 100 | 55 | 61 |
| 52 | 20 | 40 | 20 | 4 | 25 | 281 | 0.5 | 22 | 1.8 | 78 |
| 53 | 80 | 20 | 40 | 4 | 25 | 191 | 4 | 72 | 50 | 57 |
| 54 | 80 | 20 | 20 | 8 | 25 | 191 | 4 | 96 | 28 | 43 |
| 55 | 80 | 40 | 40 | 4 | 25 | 164 | 2 | 55 | 55 | 64 |
| 56 | 80 | 20 | 40 | 8 | 25 | 191 | 4 | 82 | 29 | 38 |
| 57 | 20 | 40 | 40 | 8 | 25 | 281 | 0.5 | 26 | 14 | 81 |
| 58 | 20 | 20 | 40 | 4 | 25 | 368 | 1 | 47 | 15 | 85 |
| 59 | 50 | 30 | 30 | 6 | 25 | 228 | 1.7 | 37 | 49 | 62 |
| 60 | 50 | 30 | 30 | 6 | 25 | 228 | 1.7 | 37 | 49 | 62 |
| 61 | 20 | 20 | 40 | 8 | 25 | 368 | 1 | 58 | 30 | 68 |
| 62 | 20 | 20 | 20 | 8 | 25 | 368 | 1 | 34 | 32 | 74 |
| 63 | 50 | 30 | 10 | 6 | 25 | 228 | 1.7 | 90 | 48 | 67 |
| 64 | 110 | 30 | 30 | 6 | 25 | 145 | 3.7 | 61 | 52 | 63 |
| 65 | 50 | 50 | 30 | 6 | 25 | 191 | 1 | 30 | 54 | 67 |
| 66 | 50 | 10 | 30 | 6 | 25 | 281 | 5 | 100 | 3 | 27 |
| 67 | 0 | 30 | 30 | 6 | 25 | 531 | 0 | 0 | 0 | 0 |
| 68 | 50 | 30 | 30 | 6 | 25 | 228 | 1.7 | 31 | 54 | 67 |
| 69 | 50 | 30 | 30 | 6 | 25 | 228 | 1.7 | 31 | 54 | 67 |
| 70 | 50 | 30 | 30 | 10 | 25 | 228 | 1.7 | 58 | 44 | 52 |
| 71 | 50 | 30 | 30 | 2 | 25 | 228 | 1.7 | 68 | 56 | 77 |
| 72 | 50 | 30 | 50 | 6 | 25 | 228 | 1.7 | 63 | 54 | 64 |

What is claimed is:

1. A method of preparing fluorinated organic compounds comprising contacting hydrogen fluoride with at least one compound of formula (I):

$$CX_3CXYCH_3 \quad (I)$$

where each X is independently Cl, I or Br, and each Y is independently H or F, said contacting step being carried out in the gas phase to produce a compound of formula (II)

$$CF_3CZ=CH_2 \quad (II)$$

where Z is Cl, I, Br, or F.

2. The method of claim 1 wherein said compound of formula (I) is formed by chlorinating step comprising contacting a compound of formula (III)

$$CH_nX_{3-n}CXYCH_3 \quad (III)$$

where each X is independently Cl, I or Br, each Y is independently H or F, and where n is 0, 1 or 2 with a chlorinating agent.

3. The method of claim 2 wherein said chlorinating agent comprises chlorine gas.

4. The method of claim 2 wherein said chlorinating step is conducted in the presence of light.

5. The method of claim 4 wherein said light has a wavelength of from about 250 to about 400 angstroms.

6. The method of claim 2 wherein said chlorinating step is carried out at a temperature of from about 20° C. to about 50° C.

7. The method of claim 2 wherein said chlorinating agent comprises chlorine gas and a diluent.

8. The method of claim 2 wherein said compound of formula III comprises a compound of formula (IIIA)

$$CH_3CXYCH_3 \quad (IIIA).$$

9. The method of claim 2 wherein said compound of formula III comprises a compound of formula (IIIB)

$$CH_2ClCHFCH_3 \quad (IIIB).$$

10. The method of claim 2 wherein said compound of formula III comprises a compound of formula (IIIC)

$$CH_2ClCHClCH_3 \quad (IIIC).$$

11. The method of claim 2 wherein said compound of formula III is formed by contacting propylene and/or a compound of formula (IV)

$$CH_nX_{3-n}CHC=CH_2 \quad (IV)$$

with a compound of formula $X_mY_{2-m}$
where each X is independently Cl, I or Br, and each Y is independently H or F, and wherein m is 0, 1, or 2 and provided that the compound is not $H_2$.

12. The method of claim 11 wherein said compound of formula $X_mY_{2-m}$ is HF.

13. The method of claim 11 wherein said compound of formula $X_mY_{2-m}$ is $Cl_2$.

14. The method of claim 11 wherein said compound of formula $X_mY_{2-m}$ is ClF.

15. The method of claim 11 wherein said compound of formula IV comprises propylene.

16. The method of claim 15 wherein said compound of formula $X_mY_{2-m}$ is selected from the group consisting of ClF, HF, $Cl_2$ and combinations of two or more of these.

17. The method of claim 16 wherein said compound of formula $X_mY_{2-m}$ is HF.

18. The method of claim 17 wherein said step of contacting a compound of formula IV comprises conducting at least a portion of said contacting step at a temperature of from about 70° C. to about 100° C.

19. The method of claim 17 wherein step of contacting a compound of formula IV comprises conducting at least a portion of said contacting step at a pressure of from about 5 to about 150 psia.

20. The method of claim 17 wherein said step of contacting a compound of formula IV comprises conducting at least a portion of said contacting step in the gas phase.

21. The method of claim 17 wherein said step of contacting a compound of formula IV comprises conducting at least a portion of said contacting step in the gas phase and in the presence of a catalyst.

22. The method of claim 21 wherein said catalyst comprises an iron-based catalyst.

23. The method of claim 21 wherein said catalyst comprises iron chloride.

24. The method of claim 21 wherein said catalyst comprises from about 4 to about 6 percent by weight of iron (III) chloride on a carbon support.

25. The method of claim 16 wherein said compound of formula $X_mY_{2-m}$ comprises ClF.

26. The method of claim 25 wherein said step of contacting a compound of formula IV comprises conducting at least a portion of said contacting step at a temperature of from about −95° C. to about −30° C.

27. The method of claim 25 wherein said step of contacting a compound of formula IV comprises conducting at least a portion of said contacting step at a pressure of from about 5 to about 150 psia.

28. The method of claim 25 wherein said step of contacting a compound of formula IV comprises conducting at least a portion of said contacting step in the liquid phase.

29. The method of claim 1 wherein said contacting step comprises conducting at least a portion of said contacting step at a temperature of from about 100° C. to about 600° C.

30. The method of claim 1 wherein said contacting step comprises conducting at least a portion of said contacting step at a pressure of from about 10 to about 120 psia.

31. The method of claim 1 wherein said contacting step comprises conducting at least a portion of said contacting step in the presence of a catalyst.

32. The method of claim 31 wherein said catalyst comprises nickel.

33. The method of claim 31 wherein said catalyst comprises iron chloride.

34. The method of claim 31 wherein said catalyst comprises from about 4 to about 6 percent by weight of iron (III) chloride on a carbon support.

* * * * *

UNITED STATES PATENT AND TRADEMARK OFFICE
CERTIFICATE OF CORRECTION

| | | |
|---|---|---|
| PATENT NO. | : 7,659,434 B2 | Page 1 of 1 |
| APPLICATION NO. | : 11/592415 | |
| DATED | : February 9, 2010 | |
| INVENTOR(S) | : Mukhopadhyay et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 335 days.

Signed and Sealed this

Thirtieth Day of November, 2010

David J. Kappos
*Director of the United States Patent and Trademark Office*